United States Patent [19]
Kamimura et al.

[11] 4,127,591
[45] Nov. 28, 1978

[54] METHOD OF PRODUCING MALEIC ANHYDRIDE

[75] Inventors: Shigeo Kamimura, Yamato; Tadaaki Otaki, Komae, both of Japan

[73] Assignee: Mitsubishi Chemical Industries Ltd., Tokyo, Japan

[21] Appl. No.: 753,830

[22] Filed: Dec. 23, 1976

[30] Foreign Application Priority Data

Dec. 26, 1975 [JP] Japan ............................... 50-154746
Dec. 13, 1976 [JP] Japan ............................... 51-149526

[51] Int. Cl.² .......................................... C07D 307/60
[52] U.S. Cl. .............................. 260/346.75; 252/437
[58] Field of Search .................... 260/346.8 A, 346.75

[56] References Cited

U.S. PATENT DOCUMENTS

| | | | |
|---|---|---|---|
| 3,156,706 | 11/1964 | Kerr | 260/346.8 A |
| 3,888,886 | 6/1975 | Young et al. | 260/346.8 A |
| 3,977,998 | 8/1976 | Freerks et al. | 260/346.8 A |

Primary Examiner—Henry R. Jiles
Assistant Examiner—Bernard Dentz
Attorney, Agent, or Firm—Oblon, Fisher, Spivak, McClelland & Maier

[57] ABSTRACT

A method of producing maleic anhydride by oxidizing a hydrocarbon material selected from unsaturated hydrocarbons having four or more of carbon atoms, butane and mixtures thereof with molecular oxygen or a molecular oxygen containing gas in gaseous phase and in the presence of a catalyst. The catalyst used in this method is of the type which contains vanadium, phosphorus, potassium and iron, and these components are contained in the following ratios per atom of vanadium: phosphorus, $\frac{2}{3}$ to 140 atoms; potassium, $\frac{1}{4}$ to 2 atoms; and iron, 1/10 to 70 atoms. Preferably the atomic ratio of phosphorus/iron is greater than 1.

6 Claims, No Drawings

METHOD OF PRODUCING MALEIC ANHYDRIDE

FIELD OF THE INVENTION

This invention relates to a method of producing maleic anhydride, and more particularly to the improvements in the method of producing maleic anhydride by oxidizing unsaturated hydrocarbons having four or more of carbon atoms or butane catalytically in a gaseous phase.

BACKGROUND OF THE INVENTION

It is well known that maleic anhydride can be produced by oxidizing unsaturated hydrocarbons having four or more of carbon atoms, such as butene, butadiene, cyclopentadiene, etc., with an oxygen-containing gas in the presence of a catalyst comprising vanadium pentoxide and phosphorus pentoxide (see Japanese Pat. Pub. No. 7888/1965 and U.S. Pat. No. 3,156,707).

It is also known in the art to produce maleic anhydride by oxidizing unsaturated hydrocarbons having four or more of carbon atoms in a gaseous phase by using a catalyst comprising vanadium pentoxide, phosphorus pentoxide, copper and niobium compound (U.S. Pat. No. 3,255,212), or a catalyst prepared by adding a slight amount of a compound of Group Ia elements of the Periodic Table to vanadium pentoxide and phosphorus pentoxide (U.S. Pat. No. 3,366,648), or a catalyst prepared by adding a compound of Group Ia elements of the Periodic Table to vanadium pentoxide, phosphorus pentoxide and copper (U.S. Pat. No. 3,385,796). There are also known a method using a catalyst prepared by adding iron, cobalt or nickel to a vanadium-phosphorus-oxygen type catalyst (U.S. Pat. No. 3,156,705), a method using a catalyst prepared by adding various kinds of metals such as alkali metals, iron, etc., as phosphorus stabilizer to a vanadium-phosphorus-oxygen type catalyst (U.S. Pat. No. 3,156,706), and a method using a catalyst containing an oxide of a metal selected from the group consisting of copper, silver, chromium, manganese, iron and cobalt in addition to vanadium pentoxide, phosphorus pentoxide and tungsten oxide (U.S. Pat. No. 3,478,063).

With a view to providing an industrially advantageous method for production of maleic anhydride, the present inventors have pursued various researches and experiments by adding various kinds of additives to the catalysts comprising vanadium and phosphorus oxides to determine the effects of such additives to the catalyst activity and revealed the fact that a significant improvement of the activity of the vanadium oxide - phosphorus oxide catalysts, can be attained when a specific amount of a potassium compound is added, and such finding has been applied for a patent (Japanese Pat. Pub. No. 22326/1970). The present inventors have made further studies for obtaining a still higher improvement of the catalyst activity and finally reached a finding that further addition of a specific amount of an iron compound to the above-mentioned types of catalysts can provide a more prominent improvement of the catalyst activity. This invention was attained on the basis of such finding.

SUMMARY OF THE INVENTION

The object of this invention resides in providing an industrially advantageous process for production of maleic anhydride, and such object can be attained with ease by oxidizing unsaturated hydrocarbons having four or more of carbon atoms, butane or a hydrocarbon mixture containing said substances with oxygen or an oxygen-containing gas in a gaseous phase in the presence of a catalyst which contains vanadium, phosphorus, potassium and iron and wherein said components are contained in the following atomic ratios as calculated per atom of vanadium: phosphorus, more than $\frac{2}{3}$ atom; potassium, more than $\frac{1}{4}$ atom; and iron, more than 1/10 atom. Preferably the atomic ratio of phosphorus/iron is greater than 1.

DETAILED DESCRIPTION OF THE INVENTION

The catalysts developed by the present inventors, though not definitely known in their structures, are of the type containing vanadium, phosphorus, potassium and iron as active ingredients, and it is desirable that vanadium contained therein has a valence of smaller than five.

Usually, the vanadium compounds used for preparation of the catalysts of the present invention are vanadium pentoxide and vanadates such as ammonium vanadate or other pentavalent vanadium compounds, but when using such pentavalent vanadium compounds in the method of this invention, it is desirable to reduce them into the compounds with a valence of smaller than five by introducing a reducing material such as hydrochloric acid or oxalic acid in the process of preparation of the catalyst. Of course, the compounds having already a valence of smaller than five can be favorably used without undergoing such reducing treatment. Phosphorus pentoxide is the most preferred example of the phosphorus compounds usable in the preparation of the catalyst of this invention, but it is also possible to use other various kinds of phosphoric acids or salts thereof, such as for example ammonium phosphate, potassium phosphate and iron phosphate. As for the potassium compounds used in the preparation of the catalyst of this invention, potassium hydroxide is most preferred, but other kinds of potassium compounds such as for example potassium chloride, potassium bromide, potassium carbonate, potassium bicarbonate, potassium sulfate, potassium thiosulfate, potassium hydrogensulfate, potassium hypochlorite, potassium oxalate and potassium phosphate are also usable.

Beside these three components, iron is also contained as an essential ingredient of the catalysts according to this invention. The iron compounds usable for the purpose of this invention include various kinds of ferrous and ferric compounds such as for example ferrous or ferric halide, ferrous or ferric sulfate, ferrous oxalate, ferrous citrate, ferrous or ferric phosphate, and ferrous or ferric nitrate.

For preparing the catalysts of this invention from these vanadium, phosphorus, potassium and iron compounds, it is essential that the catalyst contains these elements in the following amounts as calculated per atom of vanadium: phosphorus, more than $\frac{2}{3}$ atom, preferably within the range of 1.5 to 140 atoms although varying depending on the amount of iron and potassium; potassium, more than $\frac{1}{4}$ atom, preferably within the range of $\frac{1}{4}$ to 2 atoms; and iron, more than 1/10 atom, preferably within the range of 1/10 to 70 atoms. Preferably the atomic ratio of phosphorus/iron is preferably greater than 1.

It is to be noted that if any of the component elements in the catalyst does not exist in the above-defined ratio, for instance, if phosphorus content is less than $\frac{2}{3}$ atom per atom of vanadium, it is impossible to obtain a catalyst having satisfactory activity. Also if phosphorus exists in an amount of greater than 140 atoms per atom of vanadium, the optimum reaction temperature is elevated to make the process disadvantageous.

Likewise, if the potassium content is less than ¼ atom per atom of vanadium, no desired improvement of catalyst activity is obtained. The catalyst activity elevates gradually as the potassium content increases, but if the potassium content exceeds a certain level, the catalyst activity comes to decrease again. Therefore, it is inexpedient to have potassium contained in an amount of greater than 2 atoms per atom of vanadium.

The same holds true with iron. If the iron content is less than 1/10 atom per atom of vanadium, there is obtained little effect of addition of this element, while iron content in excess of 70 atoms results in reduced catalyst activity.

Further, the amount of phosphorus atom is preferably equal to or greater than that of iron atom and when the atomic ratio of phosphorus/iron is less than 1, the yield of maleic anhydride is lowered.

For preparing the catalyst of this invention, usually the phosphorus, potassium and iron compounds are added to a solution of a vanadium compound, for example obtained by reducing a pentavalent vanadium compound in an aqueous medium by using a reductant such as oxalic acid, and then, after evaporating water to dry the mixture, the dry mixture is calcined at a high temperature of 350° to 550° C, preferably 400° to 500° C, to thereby obtain a catalyst. The catalysts obtained according to the method of this invention can be used by supporting them on a carrier such as alumina, silica gel, titania, keiselguhr and silicon carbide. It should be noted, however, that when the catalyst component is supported on a carrier, the total content of the active ingredients in the catalyst should be greater than 5 weight %, preferably greater than 10 weight %.

Now, preparation of the catalysts used in the method of this invention is described by way of some typical embodiments. According to a preferred embodiment, a vanadium compound such as vanadium pentoxide or ammonium vanadate is suspended in water, and then a reducing material such as oxalic acid is added thereto to effect reduction under heating at 50° to 100° C, preferably 80° to 90° C, for approximately 30 minutes. This aqueous solution is then further added with a phosphorus compound such as phosphoric acid, ammonium phosphate or phosphorus pentoxide, a potassium compound such as potassium hydroxide or potassium chloride, and an iron compound such as ferrous or ferric chloride, ferrous or ferric sulfate or ferrous or ferric phosphate to react them, and the thus obtained solution is evaporated to dryness and then calcined at a predetermined temperature to thereby obtain a desired catalyst.

When it is desired to obtain a catalyst supported by a carrier, concentration of the aqueous solution in the water evaporation step is ended at a certain degree and a suitable carrier is immersed therein to impregnate the carrier with the catalyst compounds, and then the mixture is calcined at a predetermined high temperature.

It is also possible to obtain a desired carrier-supported catalyst by first supporting a pentavalent vanadium compound such as vanadium pentoxide according to a conventional method, then reducing the compound with a reducing agent such as hydrogen or sulfur dioxide gas, then impregnating the reduced compound with an aqueous solution containing a phosphorus compound such as phosphoric acid, ammonium phosphate or phosphorus pentoxide, a potassium compound such as potassium hydroxide or potassium chloride, and an iron compound such as iron chloride, iron phosphate or iron sulfate, and calcining the mixture at a predetermined high temperature.

It is desirable to employ spray drying for preparation of the catalysts used in fluidized bed reactions. In this case, it is possible to use the same materials as employed in the evaporation-to-dryness process. For obtaining a catalyst according to the spray drying process, an aqueous solution containing the vanadium, phosphorus, potassium and iron compounds is added with silica sol to obtain a slurry, then this slurry is subjected to spray drying so that the average particle size of the catalyst will range from 30 to 150 microns, and then the catalyst is calcined at a predetermined temperature. In case the iron content is high, the iron compound such as for example ferric phosphate may not necessarily be perfectly dissolved. It is desirable from respects of catalyst activity and attrition resistance of the catalyst to use silica sol such that the amount of silica in the obtained catalyst will be within the range of 70 to 25% by weight.

The carrier-supported catalysts prepared by the aforementioned immersion process can be applied to the fluidized bed reactions if the carrier particle size is beforehand regulated to suit for the fluidized bed reaction intended or by crushing the catalyst to a suitable particle size after preparation of the catalyst.

In these catalyst preparation processes, the order of addition of the component materials, that is, vanadium compound, reductant, phosphorus compound, potassium compound and iron compound, is not restricted to the one just mentioned above; no substantial difference of catalyst activity is revealed no matter what order of addition is employed for preparation of the catalyst.

It is envisaged in this invention to provide a method of producing maleic anhydride by catalytically oxidizing an unsaturated hydrocarbon having four or more of carbon atoms or butane in a gaseous phase by using a catalyst which has been prepared in the manner described above. Among the preferred examples of unsaturated hydrocarbons having four or more of carbon atoms usable as starting material for production of maleic anhydride according to the method of this invention are 1-butene, 2-butene, butadiene, mixtures thereof, and fractions having four carbon atoms obtained from cracking of naphtha. It is also possible to use unsaturated hydrocarbons having five carbon atoms such as cyclopentadiene or those having more than five carbon atoms. Aromatic hydrocarbons such as benzene can be also similarly used in the method of this invention. However, for producing desired maleic anhydride in a high yield, it is most preferable to use the unsaturated hydrocarbons having four or more of carbon atoms, particularly unsaturated aliphatic hydrocarbons such as for example 1-butene, 2-butene, butadiene or mixtures of two or more of them.

Usually, air is used as the oxidizing agent for oxidizing such hydrocarbon material, but it is of course possible to employ molecular oxygen or a mixture gas thereof with an inert gas such as nitrogen or argon gas as the oxidizer.

In order to eliminate the risk of explosion during the reaction, the mixing ratio (molar ratio) of these hydrocarbon material and oxidizer should preferably be the one lower or higher than the explosion limit, but when reacting the composition within such explosion limit, it is desirable to use a fluidized bed reactor for the sake of safety. In case the hydrocarbon material is used in excess as compared with the amount of oxidizer blended, unreacted material gas remains in the reaction product gas, so that, in such a case, it is desirable to recirculate a part of the reaction product gas for reuse.

In industrial applications of the method of this invention, it is desirable to use air as oxidizing agent, and in such a case, hydrocarbons are put to the reaction with a concentration of 0.5 to 10 vol %, preferably 1.0 to 5.0 vol %.

When using air as oxidizing agent, if the hydrocarbon material is used in excess as compared with the amount of the oxidizing agent, nitrogen contained in air is also circulated when a part of the unreacted material gas is recirculated, and the amount of nitrogen in the oxidizing agent becomes large. Such an oxidizing agent is not suitable for carrying out the oxidation reaction effectively. So that, in such a case, it is preferable to release a part of the gas when it is circulated.

For producing maleic anhydride by using the said hydrocarbon materials, oxidizer and catalyst according to the method of this invention, the material gas is introduced into the reactor charged with the catalyst at space velocity (SV) of 100 to 10,000 $hr^{-1}$, preferably 300 to 5,000 $hr^{-1}$ to effect a reaction. The reaction temperature, though somewhat varying depending on the catalyst composition, is usually within the range of 300° to 600° C, preferably 400° to 550° C.

This gaseous-phase catalytic reaction is extremely exothermic, so that it is advisable to make the catalyst particles contact with the material gas in a fluidized state in order to avoid lowering of activity due to local heating of the catalyst.

After the reaction, the obtained reaction product gas is absorbed in water or an organic solvent and then distilled or filtered according to a conventional method to obtain desired maleic anhydride.

It will be noted that the reaction product obtained by catalytic oxidation of unsaturated hydrocarbons having four or more of carbon atoms or butane in a gaseous phase according to the method of this invention is substantially composed of maleic anhydride, and the amount of by-produced saturated acids such as acetic acid are very little. There may be also by-produced aldehydes such as crotonealdehyde or acetoaldehyde, but their yields are insignificantly low. Thus, the method of this invention is capable of producing maleic anhydride in a high yield and high selectivity, and it therefore contributes greatly to industrial production of maleic anhydride.

Now the present invention is described in further detail by way of some preferred embodiments thereof, but it is to be understood that the present invention is not limited to the following embodiments but can be embodied in various other forms without departing from the scope and spirit of this invention.

EXAMPLE 1

9.1 gr (0.05 mole) of vanadium pentoxide was suspended in 100 ml of water and heated, and then 22.7 gr of oxalic acid was added gradually thereto to obtain a blue transparent solution. This solution was further added with 34.5 gr (0.30 mole) of 85% phosphoric acid, 80 ml (0.08 mole) of 1 normal potassium hydroxide and 80 ml (0.08 mole) of 1 mol/liter ferric chloride solution, and the mixture was heated and concentrated. After evaporation to dryness and crushing, the mixture was shaped and calcined in air at the temperature of 400° C for 2 hours. The obtained catalyst had the following compositional ratio (atomic ratio): V:P:K:Fe = 1:3.0:0.8:0.8.

5 ml of this catalyst was charged into a reactor made of Pyrex glass, and while maintaining the catalyst layer at the temperature of 500° C, 1-butene diluted with air to 1% concentration was passed through said catalyst layer at space velocity (SV) of 2,000 $hr^{-1}$. The conversion of 1-butene was 100%, and maleic anhydride was obtained at the yield of 63 mol % calculated on the basis of 1-butene supplied.

EXAMPLES 2-11 and Comparative Example 1-6

There were prepared catalysts with different compositional ratios according to the same process of preparation as employed in Example 1, and these catalysts were subjected to a reaction under the same reaction conditions as used in Example 1 with the reaction temperature differing in some cases. The component ratios of the respective catalysts, reaction temperature and yield of obtained maleic anhydride were as shown in Table 1 below.

Table 1

| Example | V:P:K:Fe (atomic ratio) | Reaction temp. (° C) | Yield of maleic anhydride (mol%) |
|---|---|---|---|
| 2 | 1:2.0:0.5:0.1 | 500 | 57 |
| 3 | 1:2.7:0.5:0.5 | 490 | 57 |
| 4 | 1:3.5:0.5:1.0 | 510 | 58 |
| 5 | 1:4.2:0.5:1.5 | 490 | 57 |
| 6 | 1:4.8:0.5:2.0 | 490 | 57 |
| 7 | 1:5.2:0.5:2.0 | 510 | 57 |
| 8 | 1:6.5:0.5:3.0 | 500 | 58 |
| 9 | 1:2.6:0.8:0.5 | 500 | 58 |
| 10 | 1:3.2:0.8:0.8 | 510 | 62 |
| 11 | 1:3.7:0.8:1.2 | 490 | 62 |

| Comparative Example | V:P:K:Fe (atomic ratio) | Reaction temp. (° C) | Yield of maleic anhydride (mol%) |
|---|---|---|---|
| 1 | 1:1.8:0.5:0 | 500 | 56 |
| 2 | 1:1.8:0.5:0.03 | 490 | 56 |
| 3 | 1:1.8:0:0 | 460 | 48 |
| 4 | 1:1.8:0.2:0.03 | 480 | 55 |
| 5 | 1:1.8:0.1:0.15 | 460 | 54 |
| 6 | 1:1.6:0.2:0.03 | 470 | 52 |

EXAMPLE 12

There was prepared a catalyst with the composition of V:P:K:Fe = 1:3.4:1.0:0.8 according to the same process as employed in Example 1, and 5 ml of this catalyst was charged into a reactor similar to that used in Example 1. Then, while maintaining the temperature of the catalyst layer at 500° C, 1-butene diluted with air to 2.5% concentration was passed through said catalyst layer at space velocity (SV) of 1,000 $hr^{-1}$. There was consequently obtained maleic anhydride at the yield of 59 mol % calculated on the basis of the charged 1-butene.

EXAMPLE 13

A catalyst same as prepared in Example 1 was subjected to a reaction under the same reaction conditions as practiced in Example 12 except for use of butane as hydrocarbon material and reaction temperature of 540° C. The conversion of butane was 44 mol %, and the yield of obtained maleic anhydride, as calculated on the basis of the amount of butane reacted, was 27%.

EXAMPLE 14

40.15 gr of 85 % $H_3PO_4$ was added with 60 gr of water to dilute it, and then 33.7 gr of oxalic acid was further added thereto and dissolved under heating. This solution was then added with 49.4 gr of iron phosphate (Fe: 29.4 wt %; P/Fe = 1.06 (by atomic ratio)), and the mixture was agitated under heating to obtain a uniform solution (solution A). In the meantime, 5.9 gr of vanadium pentoxide was suspended in 12 gr of water and heated, followed by gradual addition of 15.7 gr of oxalic acid, obtaining a blue solution (solution B).

Then the solution A, while agitated under heating, was added with the solution B and 5.58 gr of 85% potassium hydroxide (10 wt % aqueous solution) and then further added with 125 gr of 20 wt % silica sol.

The thus obtained solution, still agitated, was subjected to spray drying by a spray dryer to obtain the globular particles with average particle size of 50 $\mu$, and they were calcined in a muffle furnace at 500° C for one hour. The obtained catalyst had the following composition: V:K:Fe:P = 1:1.3:4:9.6 (by atomic ratio), and the weight ratio of the active ingredients to the carrier ($V_2O_5$—$K_2O$—$Fe_2O_3$—$P_2O_5$/$SiO_2$) was 65/35.

38 ml of this catalyst was charged into a reactor made of Pyrex glass with inner diameter of 23 mm, and while maintaining the temperature of the catalyst layer at 450° C, 1-butene diluted with air to 4 % concentration was passed at space velocity of 300 $hr^{-1}$ to perform a reaction while keeping the catalyst in a fluidized state. It was found that the conversion of 1-butene was 100 %, and maleic anhydride was obtained at the yield of 52 mol % based on the supplied 1-butene.

COMPARATIVE EXAMPLE 7

By following the same procedure as employed in Example 14, there was prepared a catalyst having the composition of V:P = 1:1.8 (by atomic ratio) and containing $TiO_2$ in addition to $SiO_2$ as carrier, with the weight ratio of the active ingredients to carrier being: $V_2O_5$—$P_2O_5$/$TiO_2$/$SiO_2$ = 40/35/25, and this catalyst was subjected to a reaction in a fluidized bed reactor same as used in Example 14 under the same reaction conditions as in said example but by maintaining the temperature of the catalyst layer at 460° C. The conversion of 1-butene was 100 % and the yield of maleic anhydride as calculated on the basis of the supplied 1-butene was 41 mol %.

EXAMPLE 15

9.1 gr (0.05 mole) of vanadium pentoxide was suspended in 20 ml of water and heated, and 22.7 gr of oxalic acid was added gradually thereto to obtain a blue transparent solution. (Solution A)

346 gr (1.85 moles) of ferric phosphate ($FePO_4 \cdot 2H_2O$) was mixed with 400 ml of water and 206 gr (1.79 moles) of 85% phosphoric acid. (Solution B)

3.29 gr (0.05 mole) of 85% potassium hydroxide was dissolved in 10 ml of water. (Solution C)

Solution A and Solution C were added into Solution B and further 1123 gr of silica sol solution containing 20% by weight of $SiO_2$ was added thereto and the mixture was evaporated-to-dryness under stirring and the dried mixture was crushed, shaped and calcined in air at a temperature of 500° C for 2 hours.

The atomic ratio of the catalyst components in the obtained catalyst was V : P : K : Fe = 1 : 36.4 : 0.5 : 18.5 and the weight ratio of the catalyst components : $SiO_2$ = 65 : 35.

5 ml of this catalyst was charged into a reactor made of Pyrex glass and while maintaining the catalyst layer at the temperature of 520° C, 1-butene diluted with air to 1% concentration was passed through said catalyst layer at space velocity (SV) of 1000 $hr^{-1}$. The conversion of 1-butene was 100% and the yield of maleic anhydride calculated on the basis of the supplied 1-butene was 62 mol %.

EXAMPLE 16 – 23 and Comparative Example 8 and 9

Catalysts having various atomic ratio of the catalyst components shown in the Table 2 were prepared according to the same method as described in Example 15. The reaction was carried out by using these catalysts under the same reaction condition in Example 15 except the reaction temperature was varied as shown in Table 2. The yield of maleic anhydride was also shown in Table 2.

Table 2

| Example | V:P:K:Fe (atomic ratio) | Reaction temp (° C) | Yield of maleic anhydride (mol%) |
|---|---|---|---|
| 16 | 1:16.35:0.5:8.5 | 460 | 58 |
| 17 | 1:36.35:0.5:18.5 | 500 | 61 |
| 18 | 1:30:0.5:18.5 | 490 | 59 |
| 19 | 1:66:1.0:37 | 500 | 61 |
| 20 | 1:90:1.4:50 | 500 | 60 |
| 21 | 1:126:1.7:70 | 510 | 57 |
| 22 | 1:36.4:2:18.5 | 510 | 57 |
| 23 | 1:9.6:1.3:4 | 520 | 63 |
| Comparative Example | V:P:K:Fe (atomic ratio) | Reaction temp (° C) | Yield of maleic anhydride (mol%) |
| 8 | 1:165:2.5:92.5 | 530 | 54 |
| 9 | 1:36.4:4:18.5 | 510 | 51 |

What is claimed is:

1. A method of producing maleic anhydride by oxidizing a hydrocarbon material selected from unsaturated hydrocarbons having four or more carbon atoms, butane and mixtures thereof with molecular oxygen or a gas containing molecular oxygen in a gaseous phase and in the presence of a catalyst, characterized in that the catalyst used here contains vanadium, phosphorus, potassium and iron in the form of oxides, with these ingredients being contained in the following atomic ratios calculated per atom of vanadium: phosphorus, ⅔ to 140 atoms; potassium, ¼ to 2 atoms; and iron, 1/10 to 70 atoms.

2. A method according to claim 1, wherein the hydrocarbon material is unsaturated hydrocarbons having four or more carbon atoms.

3. A method according to claim 1, wherein the hydrocarbon material is butane.

4. A method according to claim 1, wherein the reaction is carried out at such a rate that the hydrocarbon concentration will be within the range of 0.5 to 10 vol %.

5. A method according to claim 1, wherein the reaction is carried out at the temperature of 300° to 600° C.

6. A method according to claim 1, wherein the atomic ratio of phosphorus/iron in the catalyst is greater than 1.

* * * * *